(12) United States Patent
Weyl et al.

(10) Patent No.: US 6,273,432 B1
(45) Date of Patent: Aug. 14, 2001

(54) SEALING ELEMENT FOR SENSORS

(75) Inventors: Helmut Weyl, Schwieberdingen; Gerhard Schneider, Pettstadt, both of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/130,735

(22) Filed: Aug. 7, 1998

(30) Foreign Application Priority Data

Aug. 9, 1997 (DE) .............................................. 197 34 575

(51) Int. Cl.[7] ...................................................... F02F 11/00
(52) U.S. Cl. .......................... 277/591; 277/630; 277/650; 277/943; 204/424
(58) Field of Search ..................................... 277/591, 543, 277/630, 650; 73/31.05; 204/424, 426

(56) References Cited

U.S. PATENT DOCUMENTS

| 3,747,944 | * | 7/1973 | Roy et al. . |
| 3,923,667 | * | 12/1975 | Lachman . |
| 4,282,024 | * | 8/1981 | Copley et al. . |
| 4,485,182 | * | 11/1984 | Enomoto et al. . |
| 4,659,091 | * | 4/1987 | Baasner et al. . |
| 4,683,046 | * | 7/1987 | Scharpey et al. . |
| 5,301,403 | * | 4/1994 | Blank-Bewersdorff et al. . |
| 5,314,599 | * | 5/1994 | Allaire . |
| 5,397,649 | * | 3/1995 | Schienle et al. . |
| 5,700,550 | * | 12/1997 | Uyama et al. . |
| 5,846,391 | * | 12/1998 | Friese et al. . |
| 5,935,528 | * | 8/1999 | Stephenson et al. . |
| 6,025,018 | * | 2/2000 | Goldman et al. ................... 427/178 |

FOREIGN PATENT DOCUMENTS

| 195 32 090 A1 | * | 3/1997 | (DE) . |
| 195 32 090 | | 3/1997 | (DE) . |
| 59-219697 | * | 12/1984 | (JP) . |

* cited by examiner

Primary Examiner—Anthony Knight
Assistant Examiner—Alison K. Pickard
(74) Attorney, Agent, or Firm—Kenyon & Kenyon

(57) ABSTRACT

A seal for a sensor element of a gas sensor for determining the oxygen content in exhaust gases of internal combustion engines. The seal includes at least one sealing element that is inserted into a longitudinal bore of a housing and that includes a mixture of at least one ceramic compound and at least one fluoride compound.

14 Claims, 1 Drawing Sheet

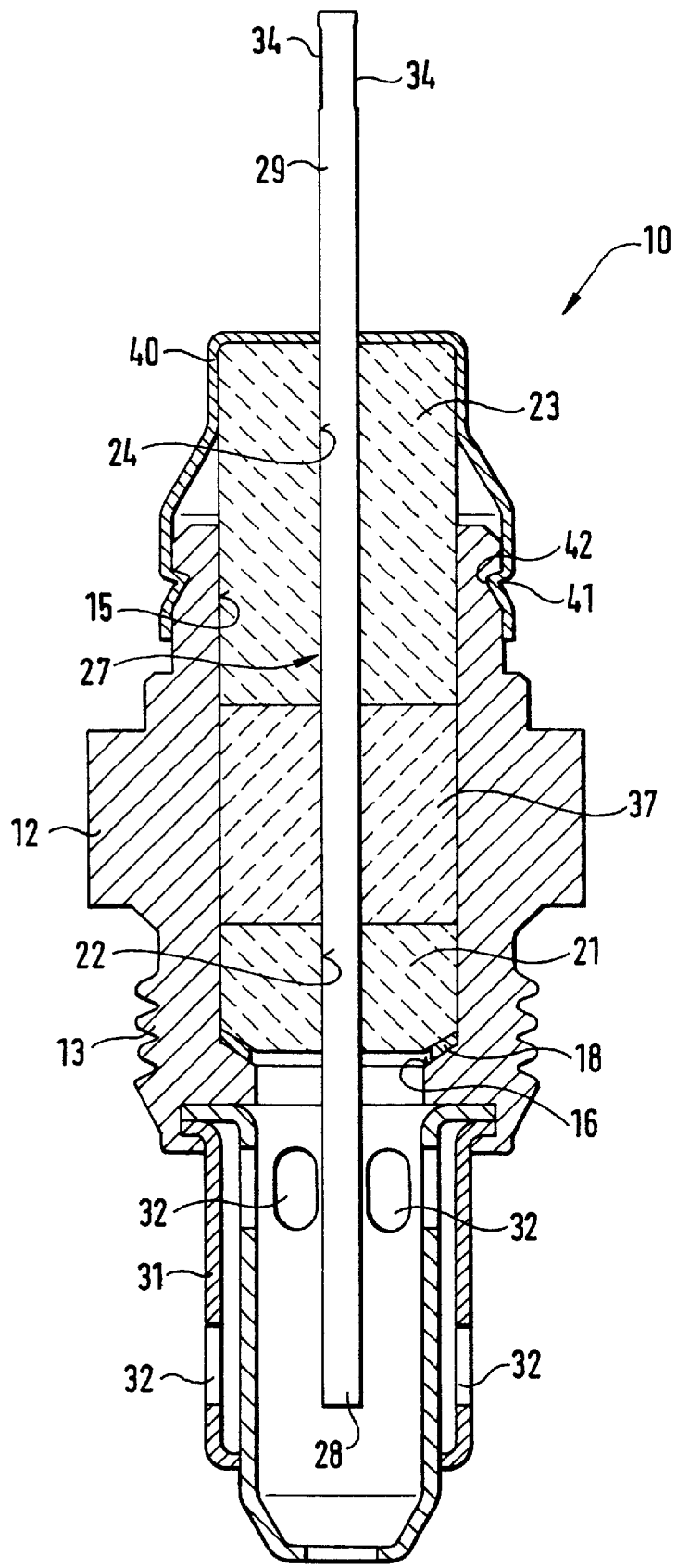

SEALING ELEMENT FOR SENSORS

FIELD OF THE INVENTION

The present invention relates to a seal for a sensor element of a gas sensor.

BACKGROUND INFORMATION

A seal for a sensor element of a gas sensor is known, for example, from German Published Patent Application No. 195 32 090 A1, in which the sensor is mounted into a longitudinal bore of a housing by way of at least two sealing members and a deformable auxiliary seal arranged between the sealing members. The two sealing members are made of magnesium aluminum silicate (steatite), and the sealing member mounted between those sealing members is made of the hexagonal allotrope of boron nitride.

SUMMARY OF THE INVENTION

The seal according to the present invention is both gas-tight and impermeable to liquids, in particular to fuels, and moreover possesses very high temperature resistance. This is achieved by way of a mixture of at least one ceramic compound and at least one fluoride compound. In addition, the use of this mixture instead of a seal configuration made up of sealing elements of different chemical compositions yields simplified handling and assembly.

In a particularly advantageous manner, steatite, i.e. the combustion product of soapstone, having the approximate chemical formula $3MgO.4SiO_2.H_2O$, in a mixture with a fluoride compound, is used as the ceramic compound. This ensures particularly high temperature stability.

In a further preferred embodiment, boron nitride is used as the ceramic compound, the hexagonal allotrope of BN being preferred. The hexagonal allotrope of boron nitride is very fine-grained and similar to its isostere graphite, a highly deformable compound, so that the tightness and flexibility of the sealing element are decisively improved.

Advantageously, a metallic fluoride, in particular a divalent or trivalent metallic fluoride, is used as the fluoride compound. The addition of a metal fluoride of this kind allows an increase in the coefficient of thermal expansion of the powder packet in temperature ranges from 500 to 1000 degrees. The coefficient of thermal expansion of the sealing element is thereby adapted to those of, for example, chromium steel or yttrium-stabilized zirconium dioxide (YSZ).

In a preferred embodiment, the quantitative concentration of the fluoride compound is 15 to 70 wt. %, in particular 20 to 30 wt. %, in terms of the total mass of the seal. By using a fluoride compound in the form of a powder having an average particle diameter $\alpha_{50}$ of 0.5 to 10 $\mu$m, in particular 1 to 5 $\mu$m, the coefficient of thermal expansion is adapted particularly well to that of YSZ. As a result of the use of the metal fluoride, the coefficient of thermal expansion (CTE) of the powder packet which is used as the sealing element is, for example, 10 to $18 \times 10^{-6}$ Kelvin$^{-1}$ in the temperature range from 500 to 1000 degrees C. The coefficient of thermal expansion of YSZ, in contrast, is $10 \times 10^{-6}$ Kelvin$^{-1}$, so that by appropriately varying the metal fluoride, the coefficient of thermal expansion can be adapted in such a way that no thermally induced stresses occur between the seal and the solid electrolyte body of the gas sensor. This makes it possible, in particular, for the powder packet of the seal to function in consistent and stable fashion even in hot gases and in continuous operation.

BRIEF DESCRIPTION OF THE DRAWING

The FIGURE shows a cross section through a gas sensor having a seal arrangement according to the present invention.

DETAILED DESCRIPTION

The FIGURE shows a gas sensor 10, for example, an electrochemical oxygen sensor, which possesses a metallic housing 12 that has threads 13 as mounting means for installation into a measured gas tube (not depicted). Housing 12 has a longitudinal bore 15 with a shoulder-shaped annular surface 16. Located on shoulder-shaped annular surface 16 is, for example, a metallic sealing ring 18 on which a measured gas-side ceramic shaped element 21 rests. Measured gas-side ceramic shaped element 21 has a continuous measured gas-side opening 22 running in the direction of longitudinal bore 15. Also arranged in longitudinal bore 15, spaced away from measured gas-side ceramic shaped element 21, is a connector-side ceramic shaped element 23. Connector-side ceramic shaped element 23 has a centrally arranged and continuous connector-side opening 24, also running in the direction of longitudinal bore 15. Measured gas-side opening 22 of measured gas-side ceramic shaped element 21 and connector-side opening 24 of connector-side ceramic shaped element 23 run in alignment with one another. Located in openings 22, 24 is a plate-shaped sensor element 27 having a measured gas-side end section 28 and a connector-side end section 29.

Measured gas-side end section 28 of sensor element 27 projects out from housing 12 and is surrounded by a protective tube 31 that is fastened to housing 12. The protective tube has entrance and exit openings 32 for the gas to be measured. Connector-side end section 29 possesses connecting contacts 34 which also project out of housing 12. Contact is made to connection contacts 34 by way of a contact plug (not depicted) equipped with connection cables. Connector-side end section 29 projecting out of housing 12 is surrounded by an encapsulation (not depicted) which protects end section 29 from environmental influences.

Located between measured gas-side ceramic shaped element 21 and connector-side ceramic shaped element 23 is a sealing element 37 consisting of a mixture consisting of a ceramic compound and a fluoride compound, for example boron nitride or steatite as the ceramic compound and calcium fluoride, magnesium fluoride, or strontium fluoride, aluminum fluoride, or yttrium fluoride, or another fluoride of the rare earths as the fluoride compound. If boron nitride is used, it is present in the form of its hexagonal allotrope. The concentration of the fluoride compound is 15 to 70 wt. %, in particular 20 to 30 wt. %, in terms of the total mass of the sealing element 37. Connector-side ceramic shaped element 23 presses onto this sealing element 37. The compressive force of connector-side ceramic shaped element 23 is applied by a metal sleeve 40. Metal sleeve 40 has, for example, multiple uniformly distributed rearward-facing prongs 41 which engage into notches 42 shaped onto housing 12. It is also possible, however, to weld metal sleeve 40 to housing 12. Sealing element 37 consisting of the ceramic-fluoride mixture is preshaped into a ring, by sintering at a low temperature of, for example, 500 degrees, before installation into longitudinal bore 15 of housing 12. The annular sealing element 37 formed in this manner is inserted, in accordance with the exemplary embodiment, into longitudinal bore 15 which already contains sensor element 27. Connector-side ceramic shaped element 23 is then arranged above sealing element 37. Metal sleeve 40 is then placed onto the connector-side ceramic shaped element. A force which acts via connector-side ceramic shaped element 23 on sealing element 37 is then exerted on metal housing 40 by way of a plunger. The prefabricated ring of sealing element 37 is thereby deformed in such a way that the material of sealing element 37 presses against sensor element 27 and housing 12.

It has been found that the sealing effect is determined substantially by the nature and concentration of the metallic fluoride compound.

The fact that a force proceeding from metal sleeve 40 acts continuously on sealing element 37 is essential to achieving tightness with respect to gas and fuel over a wide temperature range. Because the CTE is modified by the metallic fluoride, the result of a corresponding mixture of the ceramic component with the corresponding fluoride component is that the compressive force proceeding from metal sleeve 40 acts on sealing element 37 even at higher temperatures.

Utilization of sealing element 37 according to the present invention is not limited to the sealing of planar sensor elements in metallic housings. It is entirely possible also to use a sealing element 37 of this kind to seal so-called finger probes. All that is then necessary for this application is to adapt the configuration of the prefabricated ring for sealing element 37 to the geometry of the longitudinal bore and of the contact surface between the housing and the finger-shaped sensor element.

What is claimed is:

1. A seal for a sensor element of a gas sensor for determining an oxygen content in an exhaust gas of an internal combustion engine, comprising:
   a metallic housing; and
   at least one sealing element for sealing the sensor element in a longitudinal bore of the metallic housing, the at least one sealing element including a mixture of at least one ceramic compound and at least one fluoride compound.

2. The seal according to claim 1, wherein the at least one ceramic compound includes substantially steatite.

3. The seal according to claim 1, wherein the at least one ceramic compound includes substantially boron nitride.

4. The seal according to claim 1, wherein the at least one ceramic compound includes substantially a mixture of steatite and boron nitride.

5. The seal according to claim 1, wherein the at least one fluoride compound includes a metallic fluoride.

6. The seal according to claim 5, wherein the metallic fluoride includes at least one of a divalent metallic fluoride and a trivalent metallic fluoride.

7. The seal according to claim 1, wherein a quantitative concentration of the at least one fluoride compound is 15 to 70 wt. % of a total mass of the at least one sealing element.

8. The seal according to claim 1, wherein a quantitative concentration of the at least one fluoride compound is 20 to 30 wt. % of a total mass of the at least one sealing element.

9. The seal according to claim 1, wherein the at least one fluoride compound includes a powder having an average particle diameter $d_{50}$ of 0.5 to 10 μm.

10. The seal according to claim 1, wherein the at least one fluoride compound includes a powder having an average particle diameter $d_{50}$ of 1 to 5 μm.

11. The seal according to claim 1, wherein the at least one sealing element includes a deformable member and is pressed into the longitudinal bore of the metallic housing, the deformable member being deformed under a pressure such that a material of the at least one sealing element presses against the sensor element and the metallic housing.

12. The seal according to claim 1, further comprising:
   a measured gas-side ceramic shaped element arranged in the longitudinal bore of the metallic housing; and
   a connector-side ceramic shaped element arranged in the longitudinal bore of the metallic housing spaced from the measured gas-side ceramic shaped element, wherein the at least one sealing element is arranged between the measured gas-side ceramic shaped element and the connector-side ceramic shaped element.

13. The seal according to claim 12, further comprising:
   a compression element pressed onto the connector-side ceramic shaped element and joined to the metallic housing.

14. A method for manufacturing a seal for a sensor element of a gas sensor for determining an oxygen content in an exhaust gas of an internal combustion engine, the method comprising the steps of:
   providing a metallic housing; and
   arranging at least one sealing element in a longitudinal bore of the metallic housing, wherein the at least one sealing element is formed according to the steps of:
      pressing a mixture including at least one ceramic compound and at least one fluoride compound to form a shaped element,
      performing one of a heat-treating step and a sintering step on the mixture, and
      deforming the shaped element into a plurality of powder constituents under an influence of a compressive force during an assembly of the gas sensor.

* * * * *